United States Patent
Nishijima

(10) Patent No.: US 8,845,798 B2
(45) Date of Patent: Sep. 30, 2014

(54) PARTICULATE MATTER DETECTING APPARATUS FOR INTERNAL COMBUSTION ENGINE

(75) Inventor: Hiroki Nishijima, Suntou-gun (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 0 days.

(21) Appl. No.: 13/576,326

(22) PCT Filed: Dec. 7, 2010

(86) PCT No.: PCT/JP2010/071909
§ 371 (c)(1),
(2), (4) Date: Jul. 31, 2012

(87) PCT Pub. No.: WO2012/077182
PCT Pub. Date: Jun. 14, 2012

(65) Prior Publication Data
US 2012/0291632 A1    Nov. 22, 2012

(51) Int. Cl.
*B01D 49/00*    (2006.01)
*B01D 39/00*    (2006.01)
(Continued)

(52) U.S. Cl.
CPC .............. *F01N 11/00* (2013.01); *Y02T 10/47* (2013.01); *F01N 2900/1411* (2013.01); *F02D 41/029* (2013.01); *F02D 41/1467* (2013.01); *G01N 1/2252* (2013.01); *F01N 2560/05* (2013.01); *G01N 15/0656* (2013.01); *F02D 2200/0812* (2013.01); *F01N 2900/0601* (2013.01); *G01M 15/106* (2013.01)
USPC .................. 96/421; 55/522; 55/523; 55/524; 55/282.3; 422/169; 422/170; 422/171; 422/172; 422/177; 422/178; 422/179; 422/180; 422/181; 422/182; 204/415; 73/28.01; 324/693; 205/793

(58) Field of Classification Search
USPC .......................... 55/522–524, 282.3; 96/421; 422/169–172, 177–182; 204/415; 73/28.01; 324/693; 205/793; 604/415
See application file for complete search history.

(56) References Cited

U.S. PATENT DOCUMENTS

2004/0139852 A1\*  7/2004  Koga et al. ........................ 95/20
2008/0047847 A1   2/2008  Schmidt et al.
(Continued)

FOREIGN PATENT DOCUMENTS

CN    1517522 A    8/2004
JP    A-2006-266961    10/2006
(Continued)

OTHER PUBLICATIONS

Kawashima et al., English translation of JP2009-144577 Failure Determination Device for Particulate Filter, Jul. 2009, Japan.\*

(Continued)

*Primary Examiner* — Amber Orlando
(74) *Attorney, Agent, or Firm* — Oliff PLC

(57) ABSTRACT

A particulate matter detecting apparatus for an internal combustion engine that can estimate a discharge amount of the particulate matter accurately. The particulate matter detecting apparatus for an internal combustion engine, comprises: a sensor disposed at an exhaust passage of the internal combustion engine, the sensor including a pair of electrodes for detecting particulate matter in an exhaust gas; means for estimating a discharge amount of the particulate matter based on an output of the sensor, and means for acquiring a predetermined parameter that serves as an index for a rate with which the particulate matter in the exhaust gas is deposited on the sensor. The discharge amount estimating means corrects an estimated value of the discharge amount of the particulate matter based on the parameter acquired by the parameter acquiring means.

7 Claims, 7 Drawing Sheets

(51) Int. Cl.
*B01D 41/00* (2006.01)
*B01D 45/00* (2006.01)
*B01D 46/00* (2006.01)
*B01D 50/00* (2006.01)
*B01D 51/00* (2006.01)
*B01D 24/00* (2006.01)
*B01D 39/06* (2006.01)
*B01D 39/14* (2006.01)
*B01D 39/20* (2006.01)
*G01N 27/26* (2006.01)
*G01N 37/00* (2006.01)
*G01R 27/08* (2006.01)
*G01F 1/64* (2006.01)
*G01N 17/00* (2006.01)
*F01N 11/00* (2006.01)
*F02D 41/02* (2006.01)
*F02D 41/14* (2006.01)
*G01N 1/22* (2006.01)
*G01N 15/06* (2006.01)
*G01M 15/10* (2006.01)

(56) References Cited

U.S. PATENT DOCUMENTS

2009/0284271 A1   11/2009   Sakuma et al.
2010/0229629 A1    9/2010   Egami et al.

FOREIGN PATENT DOCUMENTS

| JP | A-2008-512661 | 4/2008 |
| JP | A-2009-144577 | 7/2009 |
| JP | A-2010-210539 | 9/2010 |
| WO | WO 2008/096853 A1 | 8/2008 |

OTHER PUBLICATIONS

Mar. 1, 2011 International Search Report issued in International Patent Application No. PCT/JP2010/071909 (with translation).

* cited by examiner

PARTICULATE MATTER DETECTING APPARATUS FOR INTERNAL COMBUSTION ENGINE

TECHNICAL FIELD

The present invention relates to a particulate matter detecting apparatus for an internal combustion engine.

BACKGROUND ART

JP-A-2009-144577 discloses an apparatus for determining failure of a particulate filter. This apparatus includes a particulate filter, an electric insulating material, a plurality of electrodes, and control means. More specifically, the particulate filter is disposed at an exhaust passage of an internal combustion engine. The electric insulating material is disposed downstream of the particulate filter and deposited with particulate matter (PM). The electrodes are disposed, mutually spaced apart from each other, on the electric insulating material. The control means measures an index correlated with an electric resistance value across the electrodes and, when detecting that the measured index is smaller than a predetermined reference value, determines that the particulate filter is faulty.

PRIOR ART DOCUMENTS

Patent Document

Patent Document 1: JP-A-2009-144577

SUMMARY OF THE INVENTION

Problem to be Solved by the Invention

The particulate matter detecting apparatus incorporating a PM sensor as disclosed in the abovementioned patent document estimates a discharge amount of the particulate matter as follows. Specifically, the PM sensor produces a sensor output that corresponds to electric resistance across the electrodes. The electric resistance across the electrodes reduces according to an amount of the particulate matter deposited between the electrodes. The more the discharge amount of the particulate matter, the more the amount of particulate matter deposited between the electrodes. The discharge amount of the particulate matter is estimated on the assumption of the foregoing and that the PM sensor output has a relationship that corresponds to the discharge amount of the particulate matter.

A study conducted by the inventor has, however, found that a difference may at times occur between the estimated value of the discharge amount of the particulate matter according to the above-described method and the actual discharge amount of the particulate matter depending on, for example, vehicle driving conditions.

The present invention has been made in view of the foregoing and it is an object of the present invention to provide a particulate matter detecting apparatus for an internal combustion engine that can estimate an discharge amount of the particulate matter accurately.

Solution to Problem

First aspect of the present invention is an apparatus for detecting particulate matter for an internal combustion engine, the apparatus comprising:

a sensor disposed at an exhaust passage of the internal combustion engine, the sensor including a pair of electrodes for detecting the particulate matter in an exhaust gas;

discharge amount estimating means for estimating a discharge amount of the particulate matter based on an output of the sensor; and parameter acquiring means for acquiring a predetermined parameter that serves as an index for a rate with which the particulate matter in the exhaust gas deposits on the sensor, wherein the discharge amount estimating means corrects an estimated value of the discharge amount of the particulate matter based on the parameter acquired by the parameter acquiring means.

Second aspect of the present invention is the apparatus for detecting particulate matter for an internal combustion engine according to the first aspect, wherein the predetermined parameter is an exhaust gas flow rate near the sensor.

Third aspect of the present invention is the apparatus for detecting particulate matter for an internal combustion engine according to the second aspect, wherein the sensor is an electrostatic trapping type that traps the particulate matter by attracting the particulate matter thereto using an electric field generated by application of voltage across the electrodes; and the discharge amount estimating means corrects the estimated value of the discharge amount of the particulate matter in a direction of a greater value when the exhaust gas flow rate is high, as compared when the exhaust gas flow rate is low.

Fourth aspect of the present invention is the apparatus for detecting particulate matter for an internal combustion engine according to the second aspect, wherein the sensor is an inertial trapping type that traps the particulate matter using inertia of the particulate matter that moves along an exhaust gas flow; and the discharge amount estimating means corrects the estimated value of the discharge amount of the particulate matter in a direction of a smaller value when the exhaust gas flow rate is high, as compared when the exhaust gas flow rate is low.

Fifth aspect of the present invention is the apparatus for detecting particulate matter for an internal combustion engine according to the first aspect, wherein the predetermined parameter is impedance between the electrodes.

Sixth aspect of the present invention is the apparatus for detecting particulate matter for an internal combustion engine according to the fifth aspect, wherein the discharge amount estimating means corrects the estimated value of the discharge amount of the particulate matter in a direction of a smaller value when the impedance is low, as compared when the impedance is high.

Seventh aspect of the present invention is the apparatus for detecting particulate matter for an internal combustion engine according to the fifth or the sixth aspect, further comprising:

means for resetting the sensor whereby particulate matter deposited on the sensor is burned and removed, wherein the parameter acquiring means measures the impedance when the sensor has a predetermined temperature after resetting the sensor.

Eighth aspect of the present invention is the apparatus for detecting particulate matter for an internal combustion engine according to the first aspect, further comprising:

a filter disposed at the exhaust passage, the filter for trapping particulate matter in the exhaust gas, wherein the predetermined parameter is a differential pressure between before and after the filter after a regeneration process for the filter.

Effects of the Invention

In the first aspect of the present invention, a predetermined parameter that serves as an index for the rate with which the particulate matter in the exhaust gas is deposited on the sensor is acquired and, based on the parameter acquired, the estimated value of the discharge amount of the particulate matter can be corrected. This allows an effect of a factor changing the rate at which the particulate matter in the exhaust gas is deposited on the sensor to be appropriately corrected, which enables accuracy in estimating the discharge amount of the particulate matter to be improved.

In the second aspect of the present invention, the effect from the exhaust gas flow rate near the sensor can be appropriately corrected, which enables accuracy in estimating the discharge amount of the particulate matter to be improved.

In the third aspect of the present invention, in a system incorporating a sensor of the electrostatic trapping type, the effect from the exhaust gas flow rate near the sensor can be appropriately corrected, which enables accuracy in estimating the discharge amount of the particulate matter to be improved.

In the fourth aspect of the present invention, in a system incorporating a sensor of the inertial trapping type, the effect from the exhaust gas flow rate near the sensor can be appropriately corrected, which enables accuracy in estimating the discharge amount of the particulate matter to be improved.

In the fifth aspect of the present invention, the effect from the aggregation of the electrodes or poisoning of the electrodes can be corrected appropriately by correcting the estimated value of the discharge amount of the particulate matter based on impedance between the electrodes. This enables accuracy in estimating the discharge amount of the particulate matter to be improved.

In the sixth aspect of the present invention, the effect from the aggregation of the electrodes or poisoning of the electrodes can be corrected appropriately, which enables accuracy in estimating the discharge amount of the particulate matter to be improved.

In the seventh aspect of the present invention, the effect from changes in impedance caused by temperature can be precluded by measuring the impedance when the sensor reaches a predetermined temperature. This allows an appropriate correction to be made easily.

In the eighth aspect of the present invention, the effect from the poisoning of the electrodes can be corrected appropriately based on the differential pressure between before and after the filter after the regeneration process for the filter for trapping the particulate matter. This enables accuracy in estimating the discharge amount of the particulate matter to be improved.

MODES FOR CARRYING OUT THE INVENTION

Figure 1:
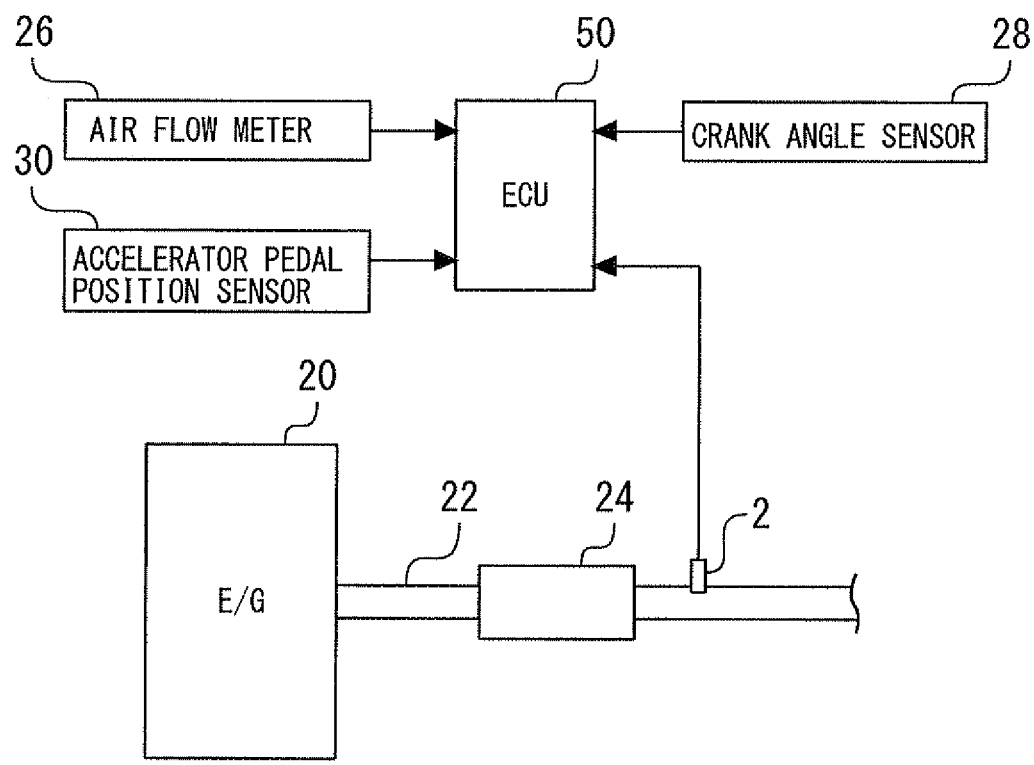
FIG. 1 is a diagram for illustrating a configuration of a system according to a first embodiment of the present invention.

Embodiments of the present invention will be described below with reference to the accompanying drawings. In the drawings, like or corresponding parts are identified by the same reference numerals and descriptions for those parts will be omitted.

First Embodiment

FIG. 1 is a diagram for illustrating a configuration of a system according to a first embodiment of the present invention. Referring to FIG. 1, the system of this embodiment includes an internal combustion engine 20. The internal combustion engine 20 is mounted as a driving power source on, for example, a vehicle. A particulate filter 24 having a function of trapping particulate matter (hereinafter may be abbreviated to a "PM") contained in an exhaust gas is disposed midway along an exhaust passage 22 of the internal combustion engine 20. A PM sensor 2 that can detect the particulate matter is disposed on the exhaust passage 22 downstream of the particulate filter 24.

The system of this embodiment further includes an electronic control unit (ECU) 50. In addition to the PM sensor 2, various types of other engine control sensors including an air flow meter 26, a crank angle sensor 28, an accelerator pedal position sensor 30 and a differential pressure sensor 32, and various types of engine control actuators including a fuel injector, not shown, are electrically connected to the ECU 50. Specifically, the air flow meter 26 detects an intake air amount of the internal combustion engine 20. The crank angle sensor 28 detects a rotational angle of an output shaft of the internal combustion engine 20. The accelerator pedal position sensor 30 detects a depression amount of an accelerator pedal (hereinafter referred to as an "accelerator pedal position") on a driver's seat of the vehicle on which the internal combustion engine 20 is mounted. The differential pressure sensor 32 detects a differential pressure between before and after the particulate filter 24.

In this embodiment, the PM sensor 2 is disposed downstream of the particulate filter 24, which allows an amount of PM discharged to the downstream side of the particulate filter 24 to be detected. If the particulate filter 24 becomes faulty, a reduced PM removal rate of the particulate filter 24 results, so that the amount of PM discharged to the downstream side of the particulate filter 24 increases greatly. In this embodiment, whether the particulate filter 24 is faulty can be accurately detected based on the PM discharge amount to the downstream side of the particulate filter 24 as detected by the PM sensor 2.

Note, however, that the position at which to dispose the PM sensor 2 in the present invention is not limited only to the downstream side of the particulate filter 24. The PM sensor 2 may be disposed, for example, at a position at which the PM discharged from the internal combustion engine 20 is directly detected.

Figure 2:
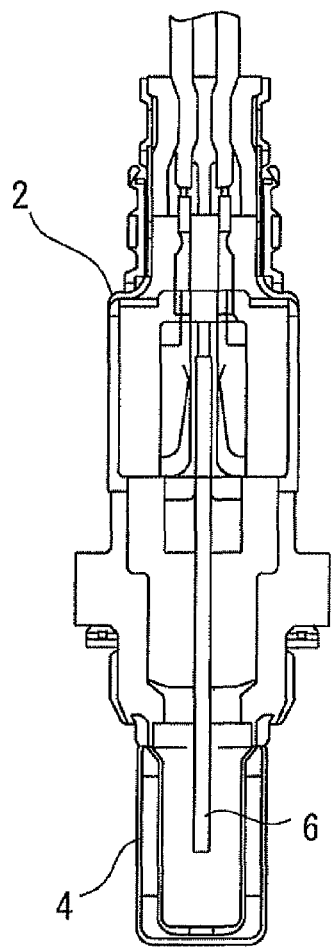
FIG. 2 is a cross-sectional view showing a PM sensor.
Figure 3:
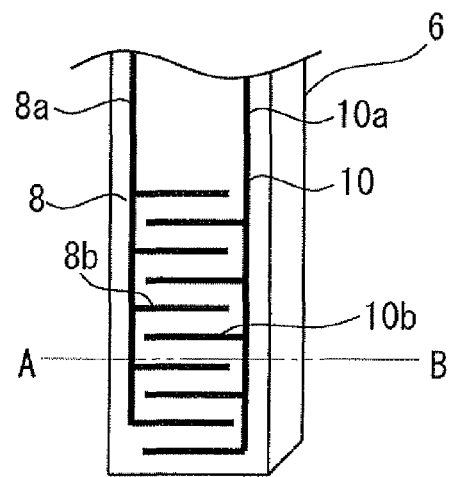
FIG. 3 is an enlarged view showing part of a sensor element section of the PM sensor.

FIG. 2 is a cross-sectional view showing the PM sensor 2. FIG. 3 is an enlarged view showing part of a sensor element section of the PM sensor 2. Referring to FIG. 2, the PM sensor 2 includes a cover 4 and an element section 6 disposed in a space inside the cover 4. The cover 4 has a plurality of holes through which gas passes. The exhaust gas flows through the multiple holes into an inside of the cover 4, so that the element section 6 is in contact with the exhaust gas.

Referring to FIG. 3, the element section 6 includes a pair of electrodes 8, 10 disposed on a surface thereof. The electrodes 8, 10 are disposed in a condition of not in contact with each other, being spaced apart from each other. Each of the electrodes 8, 10 includes a dense area in which electrodes are densely disposed as compared with other parts. More specifically, the electrodes 8, 10 include conductive parts 8a, 10a, respectively, at the other area of the dense area, the conductive parts 8a, 10a extending in a longitudinal direction of the element section 6. The dense areas near a leading end of the element section 6 include the conductive parts 8a, 10a and a plurality of conductive parts 8b, 10b formed in a direction extending perpendicularly to the conductive parts 8a, 10a. Specifically, the electrodes 8, 10 include the conductive parts 8b, 10b, respectively, each of the conductive parts 8b, 10b being arranged in a comb-like structure at the dense area of the element section 6, the comb-like structures being interdigitated with each other.

Figure 4:
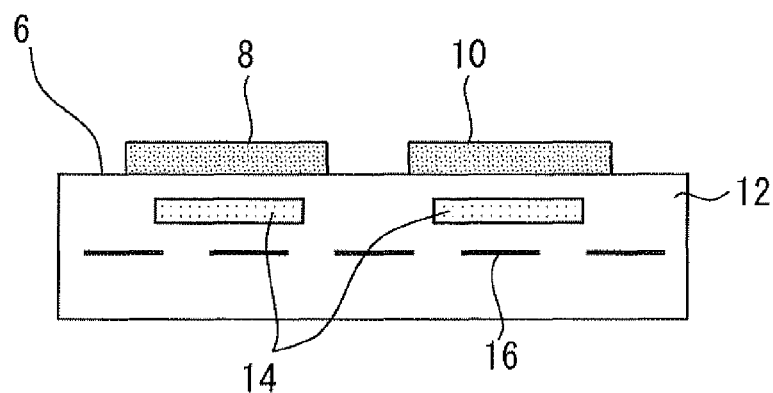
FIG. 4 is a schematic cross-sectional view taken along line A-B in FIG. 3.
Figure 5:
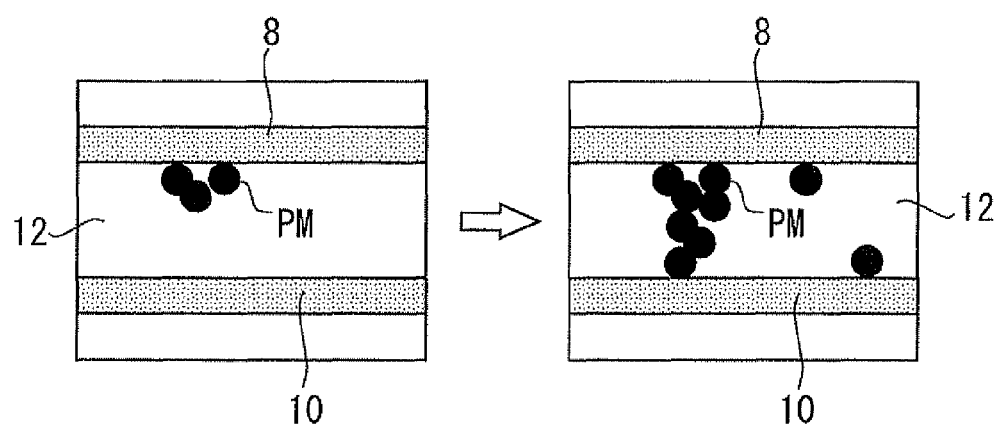
FIG. 5 illustrates schematically how PM is deposited between electrodes.

FIG. 4 is a schematic cross-sectional view taken along line A-B in FIG. 3. The upper side in FIG. 4 corresponds to a front surface side of the element section 6 in FIG. 3. FIG. 5 illustrates schematically how the PM is deposited between the electrodes 8, 10.

Referring to FIG. 4, the electrodes 8, 10 are disposed in contact with an insulating layer 12. The insulating layer 12 has a function of making the PM stick thereto. Temperature sensors 14 (temperature detecting means), such as a thermocouple, are embedded in the insulating layer 12 at positions near the electrodes 8, 10 to be associated therewith.

Each of the electrodes 8, 10 is connected via, for example, a power circuit to a power source (not shown). This allows voltage to be applied across the electrodes 8, 10. The application of the voltage generates an electric field between the electrodes 8, 10. The electric field attracts the PM charged in the exhaust gas to thereby let the PM deposit between the electrodes 8, 10 (see FIG. 5).

Each of the temperature sensors 14 is connected via a predetermined circuit to a detector (not shown) for detecting an electromotive force generated therein. The detection of the electromotive force of the temperature sensors 14 allows temperatures near the electrodes 8, 10 to be detected.

A heater 16 (heating means) is embedded in a layer beneath the temperature sensors 14. The heater 16 is formed such that a heat center thereof is disposed in a layer immediately below the dense areas of the electrodes 8, 10 to thereby ensure that the dense areas are specifically heated efficiently. The heater 16 is energized through, for example, a power circuit.

The detector, the power circuit, and the like are electrically connected to, and controlled by, the ECU 50. The PM sensor 2 outputs a sensor output that corresponds to the electric resistance across the electrodes 8, 10. The ECU 50 can detect the PM discharge amount (an amount of PM that has passed the position at which the PM sensor 2 is disposed) based on the sensor output from the PM sensor 2.

When the amount of PM deposited between the electrodes 8, 10 exceeds a predetermined limit, the PM deposited needs to be removed. According to this embodiment, energizing the heater 16 to thereby heat the element section 6 allows the amount of PM deposited between the electrodes 8, 10 to be burned and removed. Energization of the heater 16 to thereby remove the PM deposited between the electrodes 8, 10 is referred to as a "reset."

Figure 6:
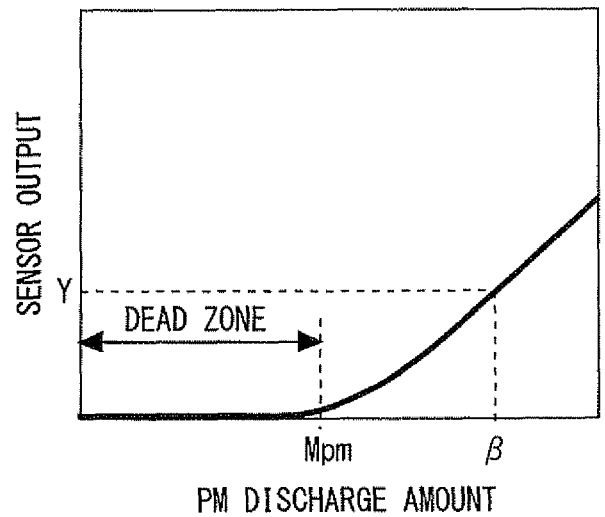
FIG. 6 is a graph showing a relationship between a sensor output of the PM sensor and an PM discharge amount.

Detection of the PM discharge amount is started in a condition in which the PM sensor 2 is reset. FIG. 6 is a graph showing a relationship between the sensor output of the PM sensor 2 when the PM discharge amount is detected and the PM discharge amount. The PM discharge amount represented by the abscissa of FIG. 6 is a total amount of PM that has passed the position at which the PM sensor 2 is disposed after the reset.

A path across the electrodes 8, 10 is insulated when the PM sensor 2 is in a reset condition. The sensor output is zero when the path across the electrodes 8, 10 is insulated. The sensor output is therefore zero in the beginnings of a detection sequence as shown in FIG. 6. The left illustration of FIG. 5 shows a condition in which, although the PM starts to deposit between the electrodes 8, 10, a conductive path is yet to be formed. In this condition, the path across the electrodes 8, 10 remains insulated, so that the sensor output remains zero. When the PM further deposits between the electrodes 8, 10 and the amount of PM deposited reaches a certain level, the PM deposited forms a conductive path between the electrodes 8, as shown in the right illustration of FIG. 5. Formation of such a conductive path reduces the electric resistance across the electrodes 8, 10, which lets the sensor output start increasing from zero. As the amount of PM deposited further increases, the conductive path becomes larger, so that the electric resistance across the electrodes 8, 10 decreases further. Thus, the sensor output increases with a decreasing electric resistance across the electrodes 8, 10.

The electric field generated by the application of the voltage across the electrodes 8, 10 causes the PM contained in the exhaust gas that flows past the position at which the PM sensor 2 is disposed to be attracted to the PM sensor 2 and deposited between the electrodes 8, 10. Therefore, the more the amount of PM moving past the position at which the PM sensor 2 is disposed (the PM discharge amount), the more the amount of PM to be deposited between the electrodes 8, 10. As a result, there is a correlation between the PM discharge amount and the amount of PM deposited between the electrodes 8, 10. Further, there is the relationship mentioned earlier between the amount of PM deposited between the electrodes 8, 10 and the sensor output. Specifically, when the amount of PM deposited between the electrodes 8, 10 reaches a predetermined level, a conductive path is formed and the sensor output starts increasing from zero. When the amount of PM deposited further increases, the sensor output increases further. Hence a relationship between the sensor output and the PM discharge amount can be assumed as shown in FIG. 6. The PM discharge amount can therefore be found based on the sensor output.

In this embodiment, the PM discharge amount when the sensor output starts increasing from zero (when the conductive path is formed) is estimated. Specifically, the PM discharge amount is estimated as follows. In the relationship shown in FIG. 6, assume that the PM discharge amount for a period of time from the completion of the reset to a point in time at which the sensor output starts increasing from zero is a predetermined value Mpm (e.g. 30 mg). After resetting the PM sensor 2 and starting a detection sequence, the ECU 50 estimates, when the sensor output starts increasing from zero, that the PM discharge amount for the period of time from the completion of the reset to the point in time at which the sensor output starts increasing from zero is Mpm.

Referring to FIG. 6, for the period of time from the reset to the point in time at which the sensor output starts increasing from zero, the sensor output remains zero and unchanged. Specifically, the period of time until the sensor output starts increasing from zero after the reset is a dead zone in which the sensor output does not respond to the PM discharge amount. In the description that follows, the period of time until the sensor output starts increasing from zero after the reset will be referred to as "dead zone time".

The method for estimating the PM discharge amount according to the present invention is not limited to that for estimating the PM discharge amount at the point in time at which the sensor output starts increasing from zero. Specifically, as shown in FIG. 6, the ECU 50 may estimate that, when the sensor output is Y, the PM discharge amount for a period of time from the completion of the reset to that particular point in time is β.

After completing the detection of the PM discharge amount as described above, the ECU 50 determines whether the amount of PM deposited between the electrodes 8, 10 reaches a level at which a reset is required based on, for example, the sensor output. If determining that the amount of PM deposited reaches the level at which a reset is required, the ECU 50 resets the PM sensor 2. After the reset of the PM sensor 2 is completed, the next sequence of detecting the PM discharge amount is started.

Figure 7:
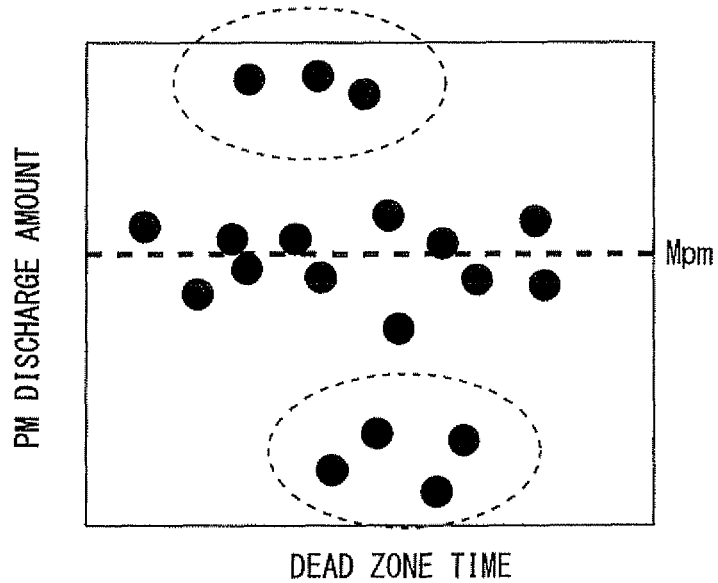
FIG. 7 is a graph showing results of an experiment for detecting the PM discharge amount using the PM sensor.

The inventor conducted an experiment for detecting the PM discharge amount using the PM sensor 2 under various driving conditions (driving modes) for the vehicle mounted with the internal combustion engine 20. In this experiment, an exhaust gas analyzer was used to measure accurately the PM discharge amount for the period of time from the completion of reset to the point in time at which the sensor output starts increasing from zero (the point in time at which a predetermined threshold value is exceeded). FIG. 7 shows results of the experiment, each of black dots representing an experimental result under each of the various driving conditions. As shown in FIG. 7, some experimental results show that the actual PM discharge amount measured with the exhaust gas analyzer is substantially consistent with the estimated value Mpm of the PM sensor 2, while others show that there is discrepancy between the two. As shown by the enclosed dotted line, in particular, there is a large discrepancy between the actual PM discharge amount and the estimated value Mpm of the PM sensor 2.

Figure 8:
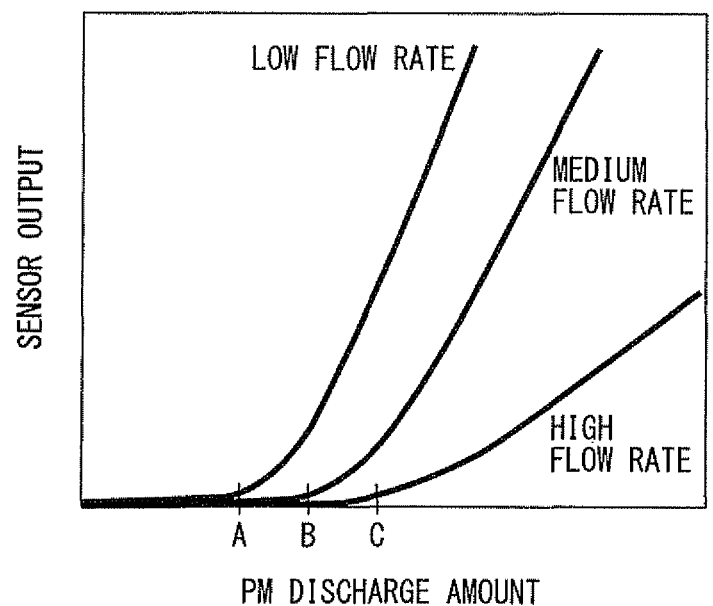
FIG. 8 is a graph showing a relationship between the sensor output of the PM sensor and the PM discharge amount when the PM discharge amount is detected with each of high, medium, and low exhaust gas flow rates.

One cause of the estimated value Mpm of the PM sensor 2 not being consistent with the actual PM discharge amount is that an exhaust gas flow rate at a position near the PM sensor 2 (hereinafter referred to simply as an "exhaust gas flow rate") varies according to the vehicle driving condition. FIG. 8 is a graph showing a relationship between the sensor output of the PM sensor 2 and the PM discharge amount when the PM discharge amount is detected with each of high, medium, and low exhaust gas flow rates. In FIG. 8, let A be the PM discharge amount when the sensor output starts increasing from zero with a relatively low exhaust gas flow rate, let C be the PM discharge amount when the sensor output starts increasing from zero with a relatively high exhaust gas flow rate, and let B be the PM discharge amount when the sensor output starts increasing from zero with a medium exhaust gas flow rate. Then, the relation of A>B>C holds.

With the PM sensor 2 of this embodiment, the electric field generated by the application of the voltage across the electrodes 8, 10 causes the PM contained in the exhaust gas to be attracted to the element section 6 and deposited between the electrodes 8, 10. At this time, the higher the exhaust gas flow rate, the smaller a rate with which the PM contained in the exhaust gas deposits between the electrodes 8, 10. This is because a higher exhaust gas flow rate accompanies a greater force of flow, so that the PM is less easily attracted to the element section 6. This results in characteristics shown in FIG. 8. Specifically, when the exhaust gas flow rate is low, the rate with which the PM contained in the exhaust gas deposits between the electrodes 8, 10 is large. A conductive path is therefore formed between the electrodes 8, 10 and the sensor output starts increasing from zero when the PM discharge amount reaches A. In contrast, when the exhaust gas flow rate is high, the rate with which the PM contained in the exhaust gas deposits between the electrodes 8, 10 is small. Therefore, a conductive path is formed between the electrodes 8, 10 and the sensor output starts increasing from zero only after the PM discharge amount reaches C (>A). When the exhaust gas flow rate is medium, the rate with which the PM contained in the exhaust gas deposits between the electrodes 8, 10 is also medium. When the PM discharge amount reaches B (A>B>C), therefore, a conductive path is formed between the electrodes 8, 10 and the sensor output starts increasing from zero.

Figure 9:
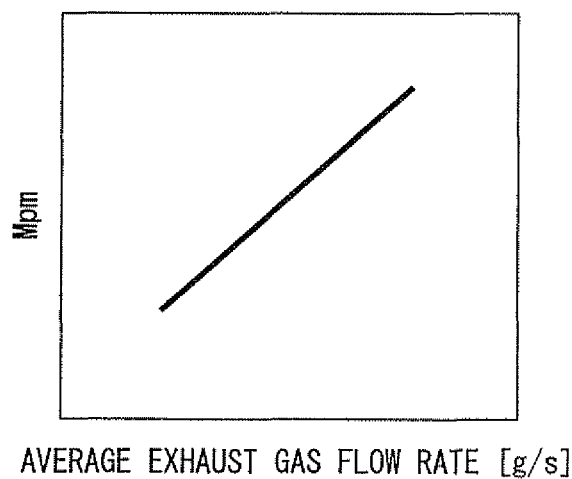
FIG. 9 is a graph showing a relationship between the estimated value Mpm of the PM discharge amount and an average exhaust gas flow rate.

To correct the effect from the exhaust gas flow rate described above, the estimated value Mpm of the PM discharge amount for the period of time from the completion of reset of the PM sensor 2 to the point in time at which the sensor output starts increasing from zero needs to be corrected as follows. Specifically, when the exhaust gas flow rate is low, the estimated value Mpm needs to be corrected to a relatively small value like A mentioned above. When the exhaust gas flow rate is high, the estimated value Mpm needs to be corrected to a relatively large value like C mentioned above. When the exhaust gas flow rate is medium, the estimated value Mpm needs to be corrected to a medium value like B mentioned above. In this embodiment, the estimated value Mpm of the PM discharge amount is to be corrected as follows. FIG. 9 is a graph showing a relationship between the estimated value Mpm of the PM discharge amount and an average exhaust gas flow rate. The average exhaust gas flow rate represented by the abscissa of FIG. 9 is an average value of exhaust gas flow rates for the period of detecting the PM discharge amount (the period of time from the completion of reset to the point in time at which the sensor output starts increasing from zero). The map shown in FIG. 9 is set such that the higher the average exhaust gas flow rate, the greater the estimated value Mpm of the PM discharge amount. For the reason described above, the effect from the exhaust gas flow rate can be appropriately corrected by correcting the estimated value Mpm of the PM discharge amount based on the map shown in FIG. 9.

A study conducted by the inventor has also found that an error may be produced of the estimated value Mpm of the PM discharge amount by aged deterioration of the PM sensor 2. The aged deterioration includes, specifically, for example, aggregation of electrodes 8, 10 and poisoning of the electrodes 8, 10. The aggregation of electrodes 8, 10 occurs when the electrodes 8, 10 are fused to be deformed as electric discharge occurs therebetween. When the aggregation of electrodes 8, 10 occurs, a spacing between the electrodes 8, 10 is narrowed, resulting in an increased intensity of the electric field produced therebetween. As a result, the force with which to attract the PM contained in the exhaust gas to the element section 6 increases, so that the rate with which the PM contained in the exhaust gas deposits between the electrodes 8, 10 increases. If the aggregation of electrodes 8, 10 occurs, therefore, a conductive path is formed and the sensor output starts increasing from zero at timing earlier than normal. Therefore, if the aggregation occurs on the electrodes 8, 10, to correct the effect of the aggregation, the estimated value Mpm of the PM discharge amount needs to be corrected in a direction of a smaller value.

The poisoning of the electrodes 8, 10, on the other hand, occurs when an insulating poisoning substance, such as what is generally called ash, is adhered and deposited between the electrodes 8, 10. When the poisoning of the electrodes 8, 10 occurs, the intensity of the electric field between the electrodes 8, 10 is reduced, so that the force with which to attract the PM contained in the exhaust gas to the element section 6 decreases. As a result, the rate with which the PM contained in the exhaust gas deposits between the electrodes 8, 10 increases. If the poisoning of the electrodes 8, 10 occurs, therefore, it takes longer for a conductive path to be formed than normal and the sensor output starts increasing from zero at timing later than normal. Therefore, if the poisoning of the electrodes 8, 10 occurs, to correct the effect of the poisoning, the estimated value Mpm of the PM discharge amount needs to be corrected in a direction of a greater value.

Figure 10:
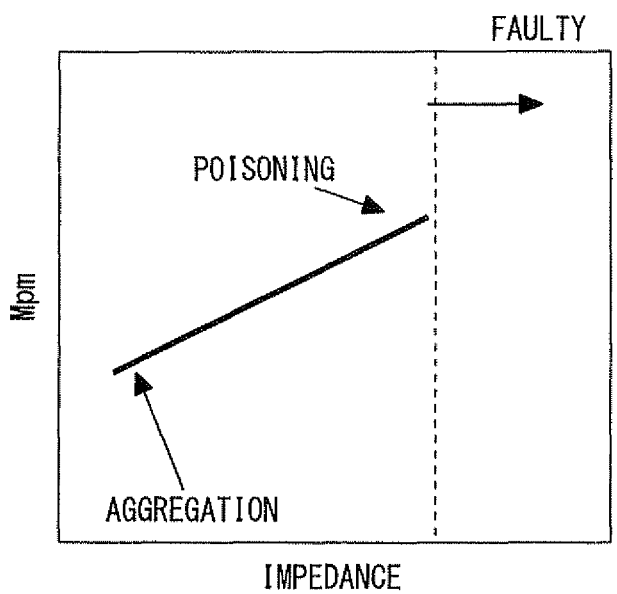
FIG. 10 is a graph showing a relationship between the estimated value Mpm of the PM discharge amount and the impedance between the electrodes.

The aggregation or poisoning of the electrodes 8, 10 can be detected by measuring impedance between the electrodes 8, 10 after resetting (hereinafter referred to simply as "impedance"). The impedance after the reset, specifically, under a condition in which the PM deposited between the electrodes 8, 10 is removed is not affected by the PM deposited and thus serves as an index representing the condition of the electrodes 8, 10. The aggregation of electrodes 8, 10 reduces the impedance, while the poisoning of the electrodes 8, 10 increases the impedance. In view of the foregoing, in this embodiment, when the impedance is lower than a normal value, it can be determined that the aggregation of electrodes 8, 10 occurs and the estimated value Mpm of the PM discharge amount is corrected in a direction of a smaller value. In contrast, if the impedance is higher than the normal value, it can be determined that the poisoning of the electrodes 8, 10 occurs and the estimated value Mpm of the PM discharge amount is corrected in a direction of a greater value. FIG. 10 is a graph showing a relationship between the estimated value Mpm of the PM discharge amount and the impedance. Referring to FIG. 10, if the impedance is low, the estimated value Mpm of the PM discharge amount is corrected in a direction of a smaller value and, if the impedance is high, the estimated value Mpm of the PM discharge amount is corrected in a direction of a greater value. The effect from the aggregation on or poisoning of the electrodes 8, 10 can thereby be appropriately corrected.

It is noted that, if the impedance is excessively high, it can be determined that an open circuit or related failure may be responsible. As shown in FIG. 10, therefore, if the impedance exceeds a predetermined limit, the PM sensor 2 may be determined to be faulty.

Figure 11:
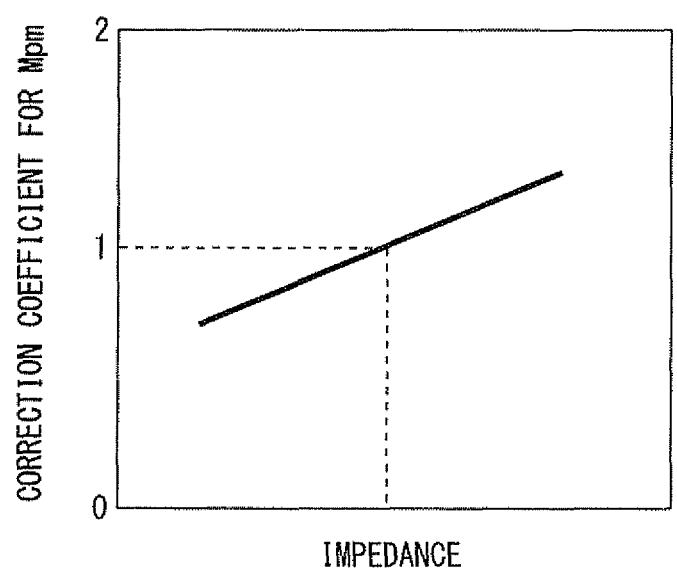
FIG. 11 is a map showing a correction coefficient for correcting the estimated value Mpm of the PM discharge amount based on the impedance between the electrodes.

FIG. 11 is a map showing a correction coefficient for correcting the estimated value Mpm of the PM discharge amount based on the impedance. The map shown in FIG. 11 represents a tendency shown in FIG. 10 converted to a corresponding correction coefficient. In this embodiment, a correction is made based on the exhaust gas flow rate and on the impedance relative to the estimated value Mpm of the PM discharge amount. The correction based on the exhaust gas flow rate is made according to the map shown in FIG. 9. The estimated value Mpm that has undergone the foregoing correction is then multiplied by the correction coefficient obtained from the map of FIG. 11, which is the correction based on the impedance.

Figure 12:
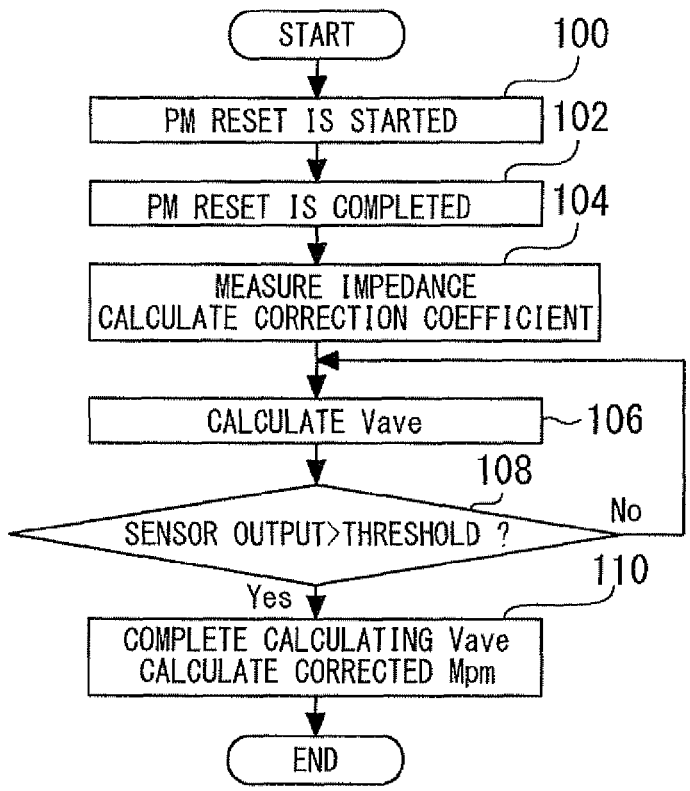
FIG. 12 is a flow chart showing a routine performed in the first embodiment of the present invention.

FIG. 12 is a flow chart showing a routine performed by the ECU 50 when the PM discharge amount is to be detected in this embodiment. In the routine shown in FIG. 12, a reset of the PM sensor 2 is started first (step 100). When PM deposited between the electrodes 8, 10 is removed, the reset of the PM sensor 2 is completed (step 102).

Next, impedance is measured (step 104). The element section 6 has a high temperature as heated by the heater 16 during the reset. After the reset is completed and the heater 16 is turned OFF, the temperature of the element section 6 starts decreasing. The impedance is measured when a temperature detected by the temperature sensor 14 is a predetermined temperature while the temperature of the element section 6 is decreasing. Impedance varies depending also on temperature. In the foregoing process, the impedance can be measured at a specific temperature for each routine. This precludes an effect from the temperature on impedance changes. When the impedance is measured, the correction coefficient is calculated from the impedance based on the map shown in FIG. 11.

After the reset of the PM sensor 2 is completed and the detection of the PM discharge amount is started, the ECU 50 sequentially calculates an average exhaust gas flow rate Vave (step 106). Specifically, the exhaust gas flow rate is calculated first based on the intake air amount detected by the air flow meter 26. Based on a history of the exhaust gas flow rate thus calculated, the average exhaust gas flow rate Vave for a period of time from the start of the detection of the PM discharge amount to a current point in time is sequentially calculated. If an exhaust temperature sensor for detecting an exhaust temperature or an exhaust pressure sensor for detecting an exhaust pressure is installed, the exhaust gas flow rate may be calculated with even higher accuracy by using also a detection value of the exhaust temperature or the exhaust pressure.

Additionally, the ECU 50 sequentially determines whether the sensor output of the PM sensor 2 exceeds a predetermined threshold value (step 108). If the sensor output exceeds the threshold value, it is determined that a change occurs in the sensor output (the sensor output starts increasing from zero). In this case, the calculation of the average exhaust gas flow rate Vave is completed and a process for calculating a corrected estimated value Mpm of the PM discharge amount (step 110). In step 110, the estimated value Mpm of the PM discharge amount for which a correction has been made against the effect from the exhaust gas flow rate is calculated based on the average exhaust gas flow rate Vave calculated and the map shown in FIG. 9. Then, the value thus calculated is multiplied by the correction coefficient based on the impedance calculated in step 104 to thereby arrive at a final estimated value Mpm of the PM discharge amount for which a correction has been made against the effect of aggregation of the electrodes or the effect of poisoning of the electrodes 8, 10.

As described heretofore, in this embodiment, the effects from the exhaust gas flow rate, and the aggregation of the electrodes or poisoning of the electrodes 8, 10 can be appropriately corrected. This enables accurate estimation of the PM discharge amount.

In the embodiment, corrections are made in terms of both the effect from the exhaust gas flow rate and from the aggregation or poisoning of the electrodes 8, 10. Nonetheless, either one of the foregoing corrections may be made for, for example, the following case. Specifically, if the PM sensor 2 is still new, it can be determined that the aggregation or poisoning of the electrodes 8, 10 is not likely to occur. In such a case, the correction in terms of the effect from the exhaust gas flow rate only is to be made. Alternatively, for an internal combustion engine that is operated under constant engine load and at a constant engine speed at all times, the correction in terms of the effect from the aggregation or poisoning of the electrodes 8, 10 only is to be made because of no changes involved in the exhaust gas flow rate.

Figure 13:
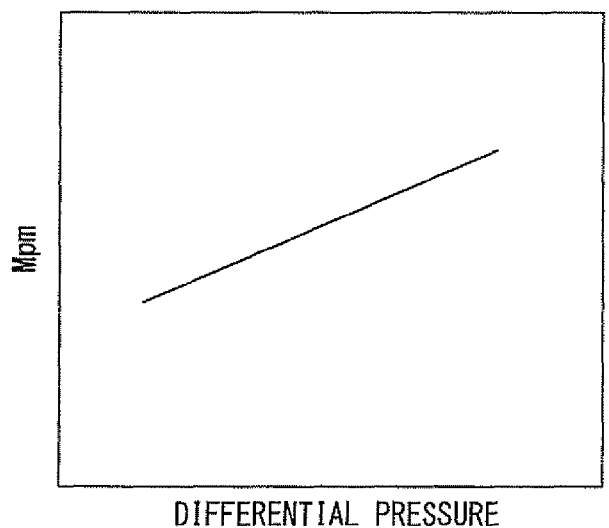
FIG. 13 is a graph showing a relationship between a differential pressure between before and after a particulate filter after a PM regeneration process, and the estimated value Mpm of the PM discharge amount.

For the correction in terms of the poisoning of the electrodes 8, 10, the following method may be employed instead of the method based on the impedance described above. When the amount of PM deposited on the particulate filter 24 increases, air-flow resistance of the particulate filter 24 increases to thereby generate a high differential pressure between before and after the particulate filter 24. In the system shown in FIG. 1, when a differential pressure detected by a differential pressure sensor 32 becomes high, it is determined that the amount of PM deposited on the particulate filter 24 is large and a PM regeneration process is performed for burning to remove the PM. The PM regeneration process is well-known and a description therefore will be omitted. When the PM regeneration process is performed and the PM deposited is removed, the differential pressure detected by the differential pressure sensor 32 is normally reduced to a normal value. The differential pressure detected by the differential pressure sensor 32 may not at times be reduced to the normal value even after the PM regeneration process. In such a case, it can then be determined that a large amount of a poisoning substance, such as ash, is deposited on the particulate filter 24. The poisoning substance is not burned at a temperature of the PM regeneration process and is not removed. As a result, even after the PM regeneration process, the air-flow resistance of the particulate filter 24 is not sufficiently reduced because of an effect from the poisoning substance deposited, so that the differential pressure detected by the differential pressure sensor 32 is high. As such, the differential pressure detected by the differential pressure sensor 32 after the PM regeneration process serves as an index indicating the amount of poisoning substance deposited on the particulate filter 24. If the particulate filter 24 is deposited with the poisoning substance, it can then be estimated that a corresponding amount of poisoning substance is deposited between the electrodes 8, 10 of the PM sensor 2. The differential pressure detected by the differential pressure sensor 32 after the PM regeneration process can therefore be used as an index indicating the poisoning of the electrodes 8, 10. Specifically, if the differential pressure detected by the differential pressure sensor 32 is high after the PM regeneration process, it can be determined that the poisoning of the electrodes 8, 10 occurs, so that the estimated value Mpm of the PM discharge amount needs to be corrected in a direction of a greater value. FIG. 13 is a graph showing a relationship between the differential pressure between before and after the particulate filter 24 after the PM regeneration process, and the estimated value Mpm of the PM discharge amount when the estimated value Mpm of the PM discharge amount is to be corrected using such a method as described above. In the map shown in FIG. 13, a correction is made such that the higher the differential pressure, the greater the estimated value Mpm of the PM discharge amount. The effect from the poisoning of the electrodes 8, 10 can thereby be corrected appropriately.

The embodiment has been described for an exemplary system that includes the PM sensor 2 of an electrostatic trapping type that traps the PM by attracting the PM to the element section 6 using the electric field generated by the application of voltage across the electrodes 8, 10. The present invention is nonetheless applicable to a system including a PM sensor of an inertial trapping type. With the PM sensor of the inertial trapping type, inertia of the PM that moves along a flow of exhaust gas causes the PM to collide with the sensor element section, which results in the PM being adhered to and deposited on the sensor element section. Therefore, the higher the exhaust gas flow rate, the faster the exhaust gas flows and the greater the PM inertia, which results in a greater rate with which the PM contained in the exhaust gas deposits on the sensor element section. Therefore, the PM sensor of the inertial trapping type is to be corrected in a direction opposite to that in which the PM sensor of the electrostatic trapping type is corrected, if the PM discharge amount is to be corrected based on the exhaust gas flow rate. Specifically, if the exhaust gas flow rate is high with the PM sensor of the inertial trapping type, the estimated value of the PM discharge amount needs to be corrected in a direction of a small value as compared with a case in which the exhaust gas flow rate is low.

The exhaust gas flow rate, impedance, and the differential pressure between before and after the particulate filter 24 in the first embodiment described above correspond to the "predetermined parameter" in the first aspect of the present invention. Similarly, the performance of the process of step 104 or 106 by the ECU 50 in the first embodiment described above achieves the "parameter acquiring means" in the first aspect of the present invention, and the performance of the process of step 110 by the ECU 50 in the first embodiment described above achieves the "discharge amount estimating means" in the first aspect of the present invention.

2 PM sensor
6 element section
8, 10 electrode
12 insulating layer
14 temperature sensor
16 heater
20 internal combustion engine
22 exhaust passage
24 particulate filter
32 differential pressure sensor
50 ECU

The invention claimed is:

1. An apparatus for detecting particulate matter for an internal combustion engine, the apparatus comprising:
    a sensor disposed at an exhaust passage of the internal combustion engine, the sensor including an insulating layer to which particulate matter in an exhaust gas can adhere and a pair of electrodes disposed in contact with the insulating layer, the sensor for detecting the particulate matter in the exhaust gas; and
    a control unit configured to perform as a discharge amount estimating means for estimating a discharge amount of the particulate matter based on an output of the sensor, wherein
    the discharge amount estimating means corrects an estimated value of the discharge amount of the particulate matter based on an exhaust gas flow rate.

2. The apparatus for detecting particulate matter for an internal combustion engine according to claim 1, wherein
    the sensor is an electrostatic trapping type that traps the particulate matter by attracting the particulate matter thereto using an electric field generated by application of voltage across the electrodes; and the discharge amount estimating means corrects the estimated value of the discharge amount of the particulate matter in a direction of a greater value when the exhaust gas flow rate is high, as compared when the exhaust gas flow rate is low.

3. The apparatus for detecting particulate matter for an internal combustion engine according to claim 1, wherein the sensor is an inertial trapping type that traps the particulate matter using inertia of the particulate matter that moves along an exhaust gas flow; and the discharge amount estimating means corrects the estimated value of the discharge amount of the particulate matter in a direction of a smaller value when the exhaust gas flow rate is high, as compared when the exhaust gas flow rate is low.

4. The apparatus for detecting particulate matter for an internal combustion engine according to claim 1, wherein the discharge amount estimating means further corrects the estimated value of the discharge amount of the particulate matter in a direction of a smaller value when impedance between the electrodes is low, as compared when the impedance is high.

5. The apparatus for detecting particulate matter for an internal combustion engine according to claim 4, further comprising:

the control unit configured to perform as a means for resetting the sensor whereby particulate matter deposited on the sensor is burned and removed; and the control unit configured to perform as a means for measuring the impedance when the sensor has a predetermined temperature after resetting the sensor.

6. The apparatus for detecting particulate matter for an internal combustion engine according to claim 1, further comprising:

a filter disposed at the exhaust passage, the filter for trapping particulate matter in the exhaust gas, wherein the discharge amount estimating means further corrects the estimated value of the discharge amount of the particulate matter in a direction of a greater value when a differential pressure between before and after the filter after a regeneration process for the filter is high, as compared when the differential pressure is low.

7. An apparatus for detecting particulate matter for an internal combustion engine, the apparatus comprising:

a sensor disposed at an exhaust passage of the internal combustion engine, the sensor including an insulating layer to which particulate matter in an exhaust gas can adhere and a pair of electrodes disposed in contact with the insulating layer, the sensor for detecting the particulate matter in the exhaust gas; and a control unit configured to perform as a discharge amount estimating device for estimating a discharge amount of the particulate matter based on an output of the sensor, wherein the discharge amount estimating device corrects an estimated value of the discharge amount of the particulate matter based on an exhaust gas flow rate.

* * * * *